United States Patent [19]

Schleifenbaum et al.

[11] 4,127,690

[45] Nov. 28, 1978

[54] FILING STRIP

[75] Inventors: Karl Schleifenbaum, Haiger; Claus Koenig, Erlangen; Wilhelm Thurmann, Obersdorf bei Siegen; Rolf Münnich, Siegen, all of Fed. Rep. of Germany

[73] Assignee: Meteor-Siegen Apparatbau Paul Schmeck, Siegen, Fed. Rep. of Germany

[21] Appl. No.: 269,237

[22] Filed: Jul. 5, 1972

[30] Foreign Application Priority Data

Jul. 5, 1971 [DE] Fed. Rep. of Germany ... 7125750[U]
Jul. 22, 1971 [DE] Fed. Rep. of Germany ... 7128183[U]

[51] Int. Cl.[2] ........................ A61F 13/02; E04F 13/20; B32B 3/14; B32B 3/04

[52] U.S. Cl. .................................... 428/40; 40/23 A; 40/360; 428/41; 428/77; 428/78; 428/101; 428/124; 428/132; 428/194; 428/906

[58] Field of Search ............... 161/102, 109, 113, 114, 161/406; 40/2 R, 23 A, 359, 360; 428/40, 41, 77, 78, 101, 124, 131, 132, 194, 906

[56] References Cited

U.S. PATENT DOCUMENTS

| | | | |
|---|---|---|---|
| 2,260,069 | 10/1941 | Whitson | 40/360 |
| 2,852,278 | 9/1958 | Dere | 428/194 |
| 3,290,809 | 12/1966 | King | 40/2 R |
| 4,017,655 | 4/1977 | Mutschler | 428/906 |

*Primary Examiner*—William R. Dixon, Jr.
*Attorney, Agent, or Firm*—Olson, Trexler, Wolters, Bushnell & Fosse, Ltd.

[57] ABSTRACT

A perforated filing strip is provided and has a self-adhesive strip thereon for attachment to a document to be filed. The perforations in the filing strip receive locating pins or the like for filing. The perforations are on an outer part of the strip and the self-adhesive strip is on the inner part of the filing strip, the inner and outer parts being defined from each other by a fold line.

3 Claims, 7 Drawing Figures

FILING STRIP

This invention concerns filing strips or adhesive strips generally.

There is known a perforated filing strip for non-perforated documents which are required to be filed by means of locating pins, tongues or the like, more particularly folded drawings, of the kind comprising an inner part intended to be secured to the document by adhesion, and a perforated outer part projecting laterally beyond the filing edge.

Such known filing strips are used to enable catalogues or the like, which cannot be completely punched, to be filed in document files. One such filing strip consists of a cardboard strip, of a length equal to that of the edge of the document facing the locating pins or tongues of the document file. When the inner strip part is secured to the document, it also reinforces the document edge concerned.

Starting from these prior-art filing strips, the invention has as one object to solve, more particularly, the problem of filing folded drawings. Standardisation of a particular fold pattern (using a residual and angular fold) has had a detrimental effect on the filing of folded drawings in the past. The disadvantages of standardised folding and of filing drawings folded in this way are uncontrollable and are as familiar as standardised folding itself.

Ordinary zig-zag folding is much less complicated, even if a residual fold is provided similarly to the standard fold system, to ensure that the writing area of the drawing is at the top. A drawing folded in this way, however, requires separate steps to enable it to be filed in files. Such a step is the fitting of a filing strip of the above kind, and one object of the invention is so to construct such a filing strip that it satisfies the requirements involved in handling and filing drawings.

To this end, in one constructional form of the invention, the strip is folded between the two parts and the outer part is adapted to be folded back over the document but can be unfolded. In this way, the strip, which preferably consists of a plastics foil, and the length of which advantageously is only relatively slightly greater than the distance between the perforations, can be moved back and forth between a filing position and a "position of rest", this being very important in the case of drawings which are frequently removed from a file for a relatively long period and can be accommodated in briefcases, envelopes or the like with the filing strip folded back into its position of rest and without being obstructed by said strip. The drawings are advantageously so folded that their finished width is less than the DIN-A-4 (21 × 29.5 cm letter size paper) width by an amount equal to the size of the outer part of the filing strip; with the filing strip unfolded they then occupy the same space in files, binders etc. as a standard-folded drawing.

To secure the filing strip by adhesion, a self-adhesive in the form of a band or strip is advantageously applied along the free longitudinal edge of the inner part, and its outer edge is preferably spaced from the outer longitudinal edge of the filing strip (on the inner part thereof). To enable the outer part of the filing strip to be accommodated in the folded-back state between the inner part and the document, the width of the inner part between the fold and the facing edge of the self-adhesive strip is advantageously somewhat greater than the width of the outer part. Since the filing strip is not connected to the document at the outermost edge of the latter, the risk of the document being torn is also reduced.

A preferred development of the invention, in which the filing strip, as part of a band consisting of a plurality of successive strips, is situated together with the self-adhesive strip on a continuous cover strip, is characterised in that the filing strip together with the cover strip has a punch hole which removes the self-adhesive strip at the point of separation from the adjacent filing strip. In this way, the adhesive is removed in the region of the separating zone without interrupting the arrangement of the filing strips or cover strip as a band. The removal of the adhesive ensures that when a filing strip is pulled away from the cover strip it does not catch owing to insufficiently separated self-adhesive strip, and prevents any disturbance particularly in the case of machine operation.

Also, particularly in cases in which the cut for separating the individual filing strip from the band is not made until immediately prior to the pulling of the filing strip away from the cover strip and its application to the document, soiling of the cutting knife by the self-adhesive is prevented.

Application of this development of the invention is not restricted to the first constructional form of filing strip described heretofore, but can advantageously be applied to other filing strips and adhesive strips generally which are arranged in the form of a band, the width of the band being less than the width of the adhesive.

In order that the invention may be well understood the two embodiments thereof, given by way of example only, will now be described with reference to the accompanying drawing, in which.

Figure 1:
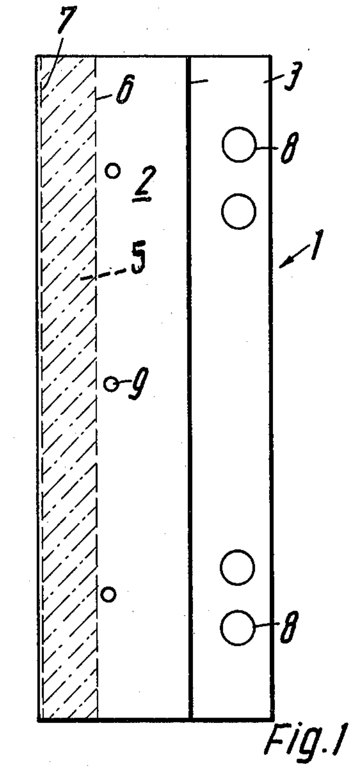
FIG. 1 is a plan view of the above-described first constructional form of filing strip in the unfolded state.
Figure 3:
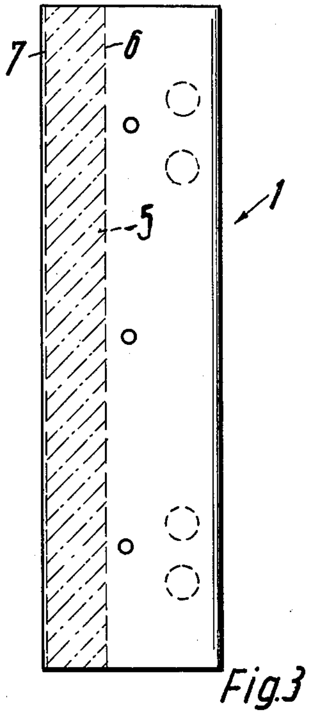
FIG. 3 is a corresponding plan view to FIG. 1 showing the filing strip in the folded condition.
Figure 2:
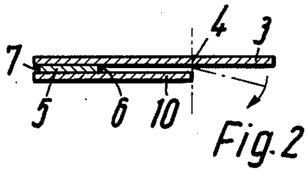
FIG. 2 is a cross-section through the filing strip shown in FIG. 1.
Figure 4:
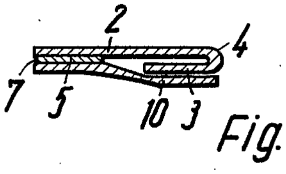
FIG. 4 is a cross-section through the folded filing strip of FIG. 3.
Figure 5:
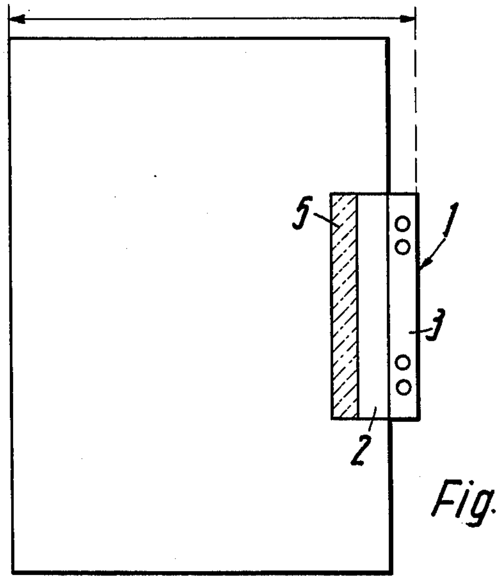
FIG. 5 is a rear view of a folded drawing with the same filing strip in the unfolded condition.

A filing strip bearing the general reference 1 consists of an inner part 2 and an outer part 3. The inner part 2 is covered by the document after it has been fitted thereto, while the outer part 3 projects beyond the edge of the document, although in the exemplified embodiment shown in FIGS. 1 to 5 this applies only to the unfolded state. In this embodiment, a fold 4 is provided between the inner part 2 and the outer part 3 and, as will be apparent from FIG. 2, enables the outer part 3 to be unfolded and folded back about the fold line. The arrangement is advantageously such that the outer part 3 is prestressed into the folded position shown in FIGS. 3 and 4, in which the part 3 bears against the part 2. Such prestressing can readily be produced if the filing strip 1 is made from a plastics material.

Self-adhesive in the form of a band 5 is applied along the free edge of the inner part 2. The edge of the band 5 adjacent the fold 4 (the inner edge) is denoted by a line 6 while the other (the outer) edge, which is spaced from the outer longitudinal edge of the strip 1, is denoted by a line 7. Before the filing strip 1 is applied to the document, a cover strip 10 of siliconised paper or the like is used to protect the adhesive band 5.

Perforations 8 serve, as usual, for locating on locating pins or the like. Holes 9 are provided to enable a sprocket wheel to feed the strip from a supply reel.

The filing strip 1 may, for example, consist of a transparent plastics material or, alternatively, be made from coloured materials, so that different coloured strips can be used for different filing purposes.

Figure 6:
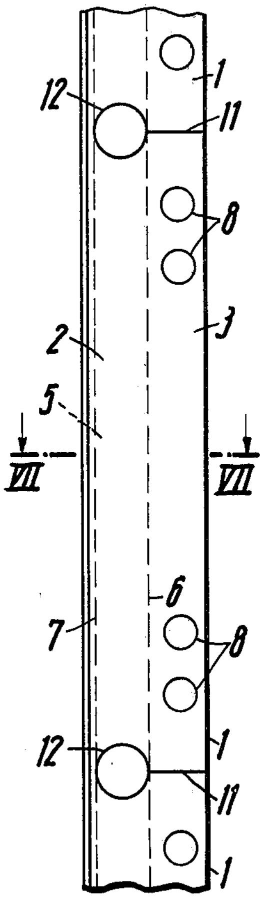
FIG. 6 is a fragmentary plan view corresponding to FIG. 1, showing the alternative embodiment in the form of a continuous strip consisting of a plurality of successive filing strips disposed on a cover strip.
Figure 7:
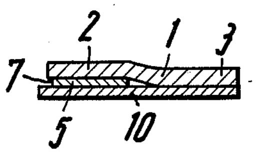
FIG. 7 is a section on the line VII—VII of FIG. 6, to a larger scale.

FIGS. 6 and 7 illustrate a development of the invention which can also be applied to other filing strips and adhesive strips generally. The individual filing strips 1 (which do not have a fold 4 and do not have an outer part 3 adapted to fold back) are disposed successively in the form of a band on the continuous cover strip 10 and are separated by cross-sections 11 which can be made either during the manufacture of the strip or just before one of the filing strips is drawn off by machine and applied. The cross-sections 11 pass through the filing strips 1 but not through the cover strip 10. In order to ensure that the self-adhesive strip 5 is also separated in the zone of the cross-sections 11, and in order to obviate soiling of the parting knives, punch holes 12 are provided of a diameter corresponding to the width of the adhesive strip 5 so as to completely remove the adhesive strip together with equal parts of the filing strips 1 and of the cover strip 10 in the region of the cross-sections 11.

What we claim is:

1. A one piece perforated filing strip for non-perforated documents which are required to be filed by means of locating pins, tongues or the like, comprising a first part adapted to be secured to the document by adhesion and bearing a self-adhesive strip thereon of less width than said first part and an adhesive-free perforated second part projecting laterally of said first part and integral therewith, the first and second parts being separated from each other by a fold line, whereby the second part is capable of being folded over said first part, the adhesive-free portion of said first part being of greater width than said second part.

2. An adhesive strip comprising a plurality of separable successive filing strip elements having a first portion, having thereon a self-adhesive coating of less width than said portion for securing each said strip element to a document, and a second portion projecting from said first portion, free of adhesive and perforated for receipt of pins or the like for locating said document, said first and second portions being of approximately equal width, said strip elements being backed by a continuous removable cover strip, the strip elements together with the cover strip being apertured at each region of separation of successive strip elements, the aperture size being such as to remove the self-adhesive coating at each such region of separation and the second portion of the strip being slit to facilitate separation of the strip elements.

3. A one piece perforated filing strip for non-perforated documents which are required to be filed by means of locating pins, tongues or the like, comprising a first part adapted to be secured to the document by adhesion and bearing a self-adhesive strip thereon, and an adhesive-free second part projecting laterally of the first part and integral therewith, said second part being of greater width than said first part.

* * * * *

UNITED STATES PATENT AND TRADEMARK OFFICE

CERTIFICATE OF CORRECTION

PATENT NO. : 4,127,690

DATED : November 28, 1978

INVENTOR(S) : Karl Schleifenbaum, Claus Koenig, Wilhelm Thurmann/ and Rolf Münnich It is certified that error appears in the above-identified patent and that said Letters Patent are hereby corrected as shown below:

Add the following to the list of references cited:

| | | | |
|---|---|---|---|
| 3,733,240 | 5/1973 | Hanke ............ | 161/102 |
| 2,994,362 | 8/1961 | Hall ............. | 161/113 |
| 2,902,734 | 9/1959 | Walters ......... | 161/406 |
| 2,264,295 | 12/1941 | Carter .......... | 161/102 |
| 3,351,514 | 11/1967 | Creigh .......... | 161/406 |
| 2,507,659 | 5/1950 | Zalkind ......... | 161/102 |
| 3,501,365 | 3/1970 | Marshall ........ | 161/113 |
| 3,070,482 | 12/1962 | Cunningham ...... | 161/406 |
| 3,535,804 | 10/1970 | Cunningham ...... | 40/2R |
| 3,444,635 | 5/1969 | Setzler ........ | 40/2R |

Signed and Sealed this

*Fifteenth* Day of *May 1979*

[SEAL]

*Attest:*

RUTH C. MASON
*Attesting Officer*

DONALD W. BANNER
*Commissioner of Patents and Trademarks*